US008958991B2

(12) United States Patent
Stephens et al.

(10) Patent No.: US 8,958,991 B2
(45) Date of Patent: *Feb. 17, 2015

(54) ANALYTE TESTING METHOD AND SYSTEM

(75) Inventors: Chris Stephens, Milpitas, CA (US); Lynne Coventry, Dundee (GB); Raymond John Welsh, Dunfermline (GB); David Angus Sturrock, Inverness (GB); Alexander Strachan, Moray (GB); Mel Chiba, San Jose, CA (US); Allan Orr, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 131 days.

This patent is subject to a terminal disclaimer.

(21) Appl. No.: 12/540,217

(22) Filed: Aug. 12, 2009

(65) Prior Publication Data

US 2010/0041084 A1 Feb. 18, 2010

Related U.S. Application Data

(60) Provisional application No. 61/089,343, filed on Aug. 15, 2008.

(51) Int. Cl.
*G01N 33/48* (2006.01)
*G01N 31/00* (2006.01)
*G06G 7/48* (2006.01)
(Continued)

(52) U.S. Cl.
CPC .......... *G01N 33/48785* (2013.01); *A61B 5/743* (2013.01); *A61B 5/7475* (2013.01); *A61B 5/14532* (2013.01)
USPC ............... 702/19; 702/22; 703/11; 703/12

(58) Field of Classification Search
CPC .............. A61B 4/14532; A61B 2562/0295; G06F 19/30; G06F 19/3412
See application file for complete search history.

(56) References Cited

U.S. PATENT DOCUMENTS 5,251,126 A 10/1993 Kahn et al.
5,507,288 A 4/1996 Bocker et al.
(Continued)

FOREIGN PATENT DOCUMENTS

CN 1818645 A 8/2006
EP 0320749 A2 6/1989
(Continued)

OTHER PUBLICATIONS

European Patent Application No. 09251990.9, Extended European Search Report dated Mar. 13, 2013, 7 pages, European Patent Office.
(Continued)

*Primary Examiner* — Larry D Riggs, II (57) ABSTRACT

Described and illustrated herein is an exemplary method of operating an analyte measurement device having a display, user interface, processor, memory, and user interface buttons. Such method can be achieved by measuring an analyte with the analyte measurement device, displaying a value representative of the analyte, querying a user to select a predetermined flag to associate the predetermined flag with the value, and pressing only one of the user interface buttons once to store the predetermined flag with the value in the memory of the analyte measurement device. In one embodiment, the testing device is a glucose meter and the analyte being tested is glucose.

20 Claims, 10 Drawing Sheets

(51) Int. Cl.
  *G06G 7/58* (2006.01)
  *G01N 33/487* (2006.01)
  *A61B 5/00* (2006.01)
  *A61B 5/145* (2006.01)

(56) References Cited

U.S. PATENT DOCUMENTS

| | | | |
|---|---|---|---|
| 7,039,560 B2 * | 5/2006 | Kawatahara et al. | 702/187 |
| 2006/0010098 A1 | 1/2006 | Goodnow et al. | |
| 2007/0016449 A1 | 1/2007 | Cohen et al. | |
| 2007/0255123 A1 | 11/2007 | Cummings et al. | |
| 2008/0034835 A1 | 2/2008 | Schell et al. | |

FOREIGN PATENT DOCUMENTS

| | | |
|---|---|---|
| EP | 0483595 | 5/1992 |
| EP | 0949506 | 10/1999 |
| EP | 1369688 A2 | 12/2003 |
| EP | 1346685 B1 | 4/2008 |
| EP | 2085029 A1 | 8/2009 |
| GB | 2389419 A | 12/2003 |
| GB | 2443434 | 5/2008 |
| JP | 2004154547 A | 6/2004 |
| JP | 2007117434 A | 5/2007 |
| JP | 2008526320 A | 7/2008 |
| JP | 2008531994 A | 8/2008 |
| TW | 200817676 A1 | 4/2008 |
| WO | WO 97/08605 A2 | 3/1997 |
| WO | WO 2004/023972 A2 | 3/2004 |
| WO | WO 2005/011952 A2 | 10/2005 |
| WO | WO 2005/093629 A2 | 10/2005 |
| WO | WO 2006/037802 A2 | 4/2006 |
| WO | 2006072035 A1 | 7/2006 |
| WO | WO 2006/072035 A1 | 7/2006 |
| WO | WO 2006072035 A1 * | 7/2006 |
| WO | 2006091561 A1 | 8/2006 |
| WO | WO 2006/091564 A1 | 8/2006 |
| WO | WO 2007019289 A1 * | 2/2007 |
| WO | WO 2008/060827 A2 | 5/2008 |
| WO | WO 2008/106070 A2 | 9/2008 |

OTHER PUBLICATIONS

Patent Examination Report issued in related Australian Patent Application No. 2009208141, dated Jan. 13, 2014, 3 pages.
First Office Action issued in related Chinese Patent Application No. 200910173367.2, dated May 24, 2013, 22 pages.
Second Office Action issued in related Chinese Patent Application No. 200910173367.2, dated Feb. 19, 2014, 22 pages.
Third Office Action issued in related Chinese Patent Application No. 200910173367.2, dated Jun. 26, 2014, 24 pages.
Search Report issued in related Chinese Patent Application No. 200910173367.2, dated Apr. 7, 2013, 2 pages.
Notification of Defects issued in related Israeli Patent Application No. 200352, dated Oct. 29, 2013, 4 pages.
Search Report issued in related Taiwan Patent Application No. 98127326, dated Apr. 3, 2014, 9 pages.
Notification of Reasons for Refusal issued in related Japanese Patent Application No. 2009-187958, dated Nov. 19, 2013, 11 pages.

* cited by examiner

ANALYTE TESTING METHOD AND SYSTEM

PRIORITY

This patent application claims the benefit of priority under the applicable provisions of 35 USC §§119, 120, 363 and 365 from U.S. Provisional Patent Application Ser. No. 61/089,343 filed on Aug. 15, 2008, which prior application is incorporated herein by reference in its entirety.

BACKGROUND

Glucose monitoring is a fact of everyday life for diabetic individuals. The accuracy of such monitoring can significantly affect the health and ultimately the quality of life of the person with diabetes. Generally, a diabetic patient measures blood glucose levels several times a day to monitor and control blood sugar levels. Failure to test blood glucose levels accurately and on a regular basis can result in serious diabetes-related complications, including cardiovascular disease, kidney disease, nerve damage and blindness. There are a number of electronic devices currently available which enable an individual to test the glucose level in a small sample of blood. One such glucose meter is the OneTouch® Profile™ glucose meter, a product which is manufactured by LifeScan.

In addition to glucose monitoring, diabetic individuals often have to maintain tight control over their lifestyle, so that they are not adversely affected by, for example, irregular food consumption or exercise. In addition, a physician dealing with a particular diabetic individual requires detailed information on the lifestyle of the individual to provide effective treatment or modification of treatment for controlling diabetes. Currently, one of the ways of monitoring the lifestyle of an individual with diabetes has been for the individual to keep a paper logbook of their lifestyle. Another way is for an individual to simply rely on remembering facts about their lifestyle and then relay these details to their physician on each visit.

The aforementioned methods of recording lifestyle information are inherently difficult, time consuming, and possibly inaccurate. Paper logbooks are not necessarily always carried by an individual and may not be accurately completed when required. Such paper logbooks are small and it is therefore difficult to enter detailed information requiring detailed descriptors of lifestyle events. Furthermore, an individual may often forget key facts about their lifestyle when questioned by a physician who has to manually review and interpret information from a hand-written notebook. There is no analysis provided by the paper logbook to distil or separate the component information. Also, there are no graphical reductions or summary of the information. Entry of data into a secondary data storage system, such as a database or other electronic system, requires a laborious transcription of information, including lifestyle data, into this secondary data storage. Difficulty of data recordation encourages retrospective entry of pertinent information that results in inaccurate and incomplete records.

Moreover, a diabetic individual often has to keep a plurality of devices on their person for diagnosis and treatment, for example both glucose level monitoring equipment and medication. Hence, having to carry paper records of their lifestyle is an added unwanted burden and entry of data therein is very time consuming.

There currently exist a number of portable electronic devices that can measure glucose levels in an individual and store the levels for recalling or uploading to another computer for analysis. One such device is the Accu-Check™ Complete™ System from Roche Diagnostics, which provides limited functionality for storing lifestyle data. However, the Accu-Check™ Complete™ System only permits a limited selection of lifestyle variables to be stored in a meter. There is no intelligent feedback from values previously entered into the meter and the user interface is unintuitive for an infrequent user of the meter.

SUMMARY OF THE DISCLOSURE

Applicants have recognized a need for an electronic device for logging and analyzing lifestyle data, which does not increase the number of devices an individual has to keep on their person. Such device must be also more intuitive and easier to use than other devices, thereby encouraging an individual to record information related to their lifestyle. Lifestyle data should be taken to mean any quantifiable information, which might affect or represent an individual's physical condition. Examples of lifestyle data are food consumption, physical exertion (e.g. exercise), medication intake and health checks performed on the individual.

In view of the foregoing and in accordance with one aspect, there is provided a method of operating an analyte measurement device having a display, user interface, processor, memory and user interface buttons, the method can be achieved by measuring an analyte with the analyte measurement device; displaying a value representative of the analyte; presenting one of a plurality of predetermined flags; querying a user to select the predetermined flag to associate the flag with the value; and pressing only one of the user interface buttons once to store the predetermined flag with the value in the memory of the device.

The user interface buttons may include an up button, a down button, and an OK button; the plurality of predetermined flags may include a before meal flag, an after meal flag, a fasting flag, or a blank flag; the querying can include pressing a user interface button to select another of the plurality of predetermined flags; the querying may include always querying a user whenever a measuring step has been completed; the querying may include querying a user whenever a measuring step indicates that an analyte value is outside a predetermined range; the pressing may include storing in memory the date and time at the completion of the measuring step along with the selected flag.

In one variation, the measuring may include inserting a test strip into a strip port provided by the measurement device; and depositing a blood sample on a testing portion of the test strip without entering a calibration parameter for the test strip.

In another variation, the measuring may include inserting a test strip into a strip port provided by the measurement device; inputting a calibration parameter for the test strip via the user interface buttons of the device; and depositing a blood sample on a testing portion of the test strip; the inserting may include turning on the measurement device when the strip is fully inserted into the strip port.

In an embodiment, the plurality of predetermined flags comprise a comment title, a plurality of comments, comment page number, no comment, not enough food, too much food, mild exercise, strenuous exercise, medication, stress, illness, hypoglycemic state, menses, vacation, and combinations thereof; and in another variation, a plurality of menus is displayed. In one variation, one of a plurality of menus may include a prompt for last result, all results, averages, and settings.

In an embodiment, a plurality of menus comprises a prompt for all results average, meal averages, and fasting averages.

In an embodiment, displaying comprises exhibiting a message of a value less than a predetermined value.

In an embodiment, displaying comprises exhibiting a message of a value higher than a predetermined value.

In an embodiment, pressing comprises storing the predetermined flag with the message.

In yet another embodiment, a glucose measurement device is provided that may include a glucose measurement unit, display, processor and memory. The measurement unit is configured to provide signals indicative of glucose amount in a fluid sample. The processor is coupled to the display, glucose measurement unit, memory and user interface buttons so that, upon receipt of signals representing a glucose amount in a fluid sample from the measurement unit, the display exhibits one of a plurality of predetermined flags and the user interface buttons are operable to associate the one predetermined flag with the glucose amount in the memory with only one of the user interface buttons.

In view of the foregoing and in accordance with another aspect, there is provided a method of operating an analyte measurement device having a display, user interface, processor, memory and user interface buttons, the method can be achieved by measuring an analyte with the analyte measurement device; displaying a value representative of the analyte; querying a user to select a predetermined flag to associate the predetermined flag with the value whenever the measuring is completed; ignoring activation of any of the user interface buttons except for a selected button; and associating the value with the predetermined flag upon activation of the selected button in the memory of the device.

In an embodiment, querying comprises repetitively flashing on the display an icon representative of the selected user interface buttons to prompt a selection of such user interface button.

These and other embodiments, features and advantages will become apparent to those skilled in the art when taken with reference to the following more detailed description of the invention in conjunction with the accompanying drawings that are first briefly described.

BRIEF DESCRIPTION OF THE FIGURES

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which.

DETAILED DESCRIPTION OF THE FIGURES

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
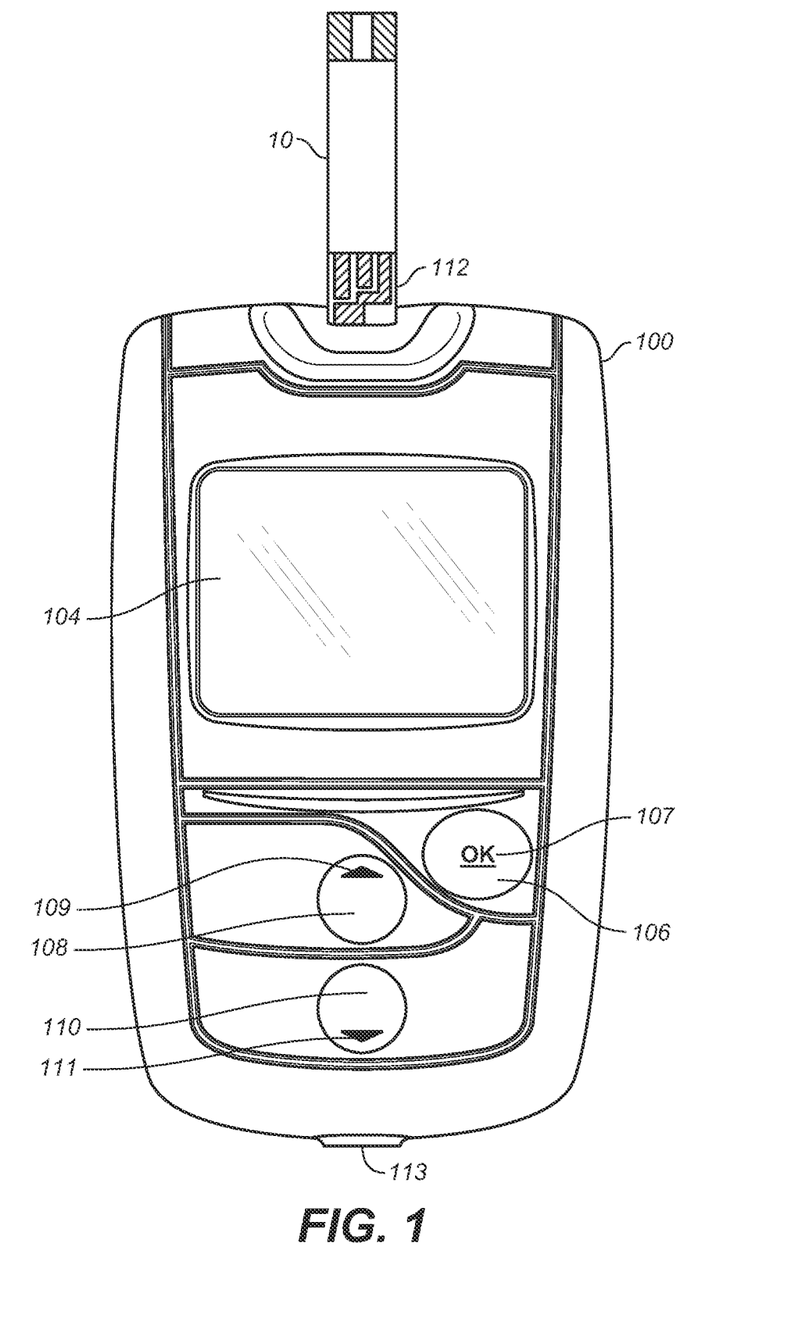
FIG. 1 is an exemplary plan view of an analyte measurement device, according to an embodiment.

FIG. 1 illustrates an analyte measurement device 100, for testing glucose levels in the blood of an individual. Analyte measurement device 100 may include user interface buttons (106, 108, 110) for entry of data, navigation of menus, and execution of commands. Data can include values representative of analyte concentration, and/or information, which are related to the everyday lifestyle of an individual. Information, which is related to the everyday lifestyle, can include food intake, medication use, the occurrence of health check-ups and general health condition and exercise levels of an individual. Analyte measurement device 100 also may include display 104. Display 104 can be used to report measured glucose levels, and to facilitate entry of lifestyle related information.

Analyte measurement device 100 may include first user interface button 106, second user interface button 108, and third user interface button 110. User interface buttons 106, 108, and 110 facilitate entry and analysis of data stored in the testing device, enabling a user to navigate through the user interface displayed on display 104. User interface buttons 106, 108, and 110 include first marking 107, second marking 109, and third marking 111, which help in correlating user interface buttons to characters on display 104.

Analyte measurement device 100 can be turned on by inserting a test strip 10 into data port 113, by pressing and briefly holding first user interface button 106, or when data traffic is detected across data port 113. Analyte measurement device 100 can be switched off by removing the test strip 10, pressing and briefly holding first user interface button 106, navigating to and selecting a meter off option from a main menu screen, or by not pressing any buttons for a predetermined time. Display 104 can optionally include a backlight.

Data port 113 accepts a suitable connector attached to a connecting lead, thereby allowing analyte measurement device 100 to be linked to an external device such as a personal computer. Data port 113 can be any port that allows for transmission of data (serial or parallel) such as, for example, serial or parallel port in wired or wireless form. A personal computer, running appropriate software, allows entry and modification of set-up information (e.g. the current time, date, and language), and can perform analysis of data collected by analyte measurement device 100. In addition, the personal computer may be able to perform advanced analysis functions, and/or transmit data to other computers (i.e. over the internet) for improved diagnosis and treatment. Connecting analyte measurement device 100 with a local or remote computer facilitates improved treatment by health care providers.

Figure 2:
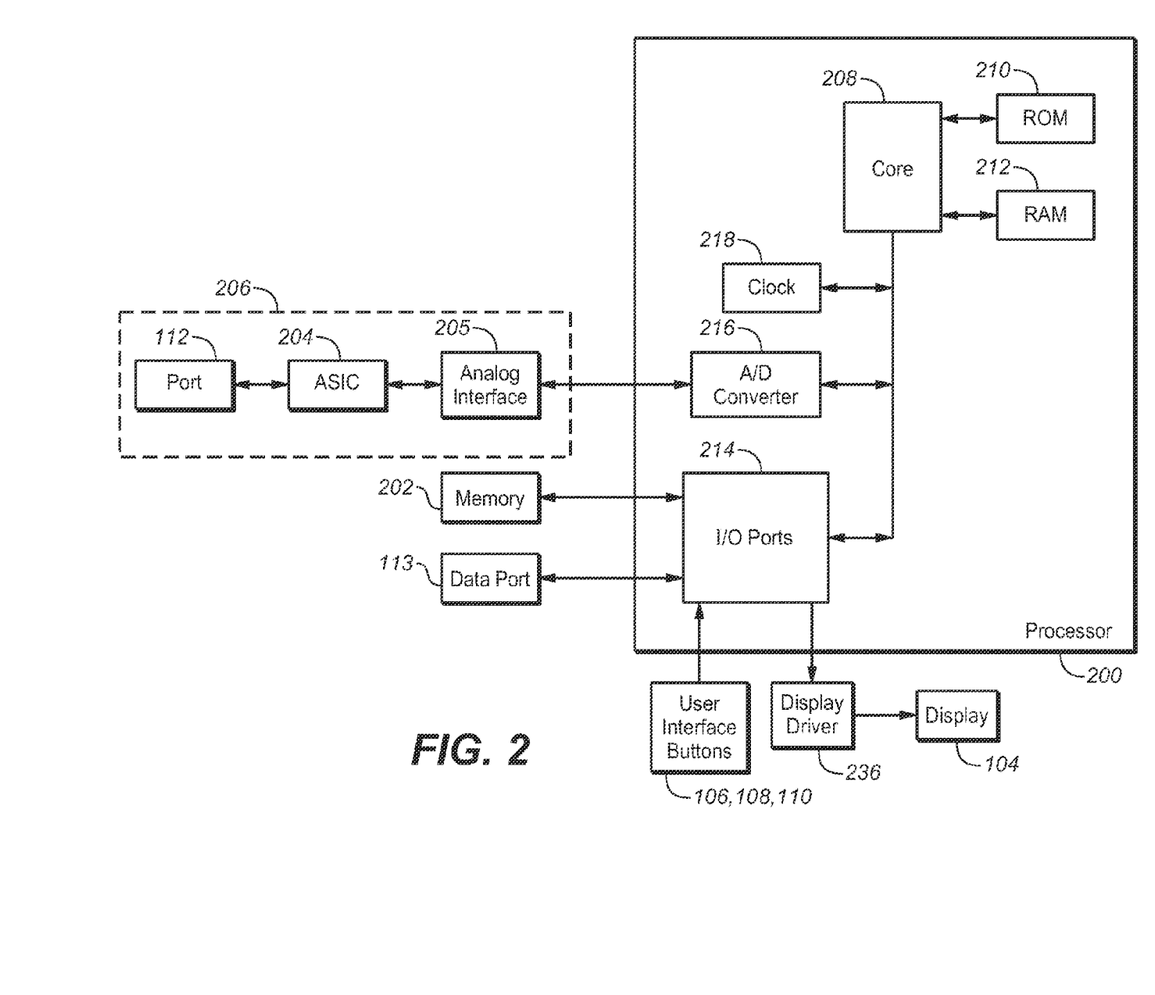
FIG. 2 is an exemplary block diagram illustrating the principal internal components of an analyte measurement device, according to an embodiment.

Referring to FIG. 2, an exemplary internal layout of analyte measurement device 100 is shown. Analyte measurement device 100 may include a processor 200, which in some embodiments described and illustrated herein is a 32-bit RISC microcontroller. In other embodiments described and illustrated herein, processor 200 is selected preferably from the MSP 430 family of ultra-low power microcontrollers manufactured by Texas Instruments of Dallas, Tex. The processor can be bi-directionally connected via I/O ports 214 to memory 202, which in some embodiments described and illustrated herein is an EEPROM. Also connected to processor 200 via I/O ports 214 are the data port 113, the user interface buttons 106, 108, and 110, and a display driver 236. Data port 113 can be connected to processor 200, thereby enabling transfer of data between memory 202 and an external device, such as a personal computer. User interface buttons 106, 108, and 110 are directly connected to processor 200. Processor 200 controls display 104 via display driver 236.

In embodiments described and illustrated herein, analyte measurement device 100 may include an Application Specific Integrated Circuit (ASIC) 204, providing electronic circuitry used in measurements of glucose level in blood that has been applied to a test strip 10 inserted into strip port 112. Analog voltages can pass to and from ASIC 204 by way of analog interface 205. Analog signals from analog interface 205 can be converted to digital signals by A/D converter 216. Port 112, ASIC 204 and Analog Interface 205 constitute exemplarily an analyte measurement unit 206 that provides data regarding analyte from a biological fluid sample deposited on strip 10. Processor 200 further comprises core 208, ROM 210 (containing computer code), RAM 212, and clock 218. In one embodiment, the processor 200 is configured (or programmed) to disable all of the user interface buttons except for a single button upon a display of an analyte value by the display unit such as, for example, during a time period after an analyte measurement. Where desired, the processor 200 is configured (or programmed) to ignore any input from all of the user interface buttons except for a single button upon a display of an analyte value by the display unit.

Figure 3:
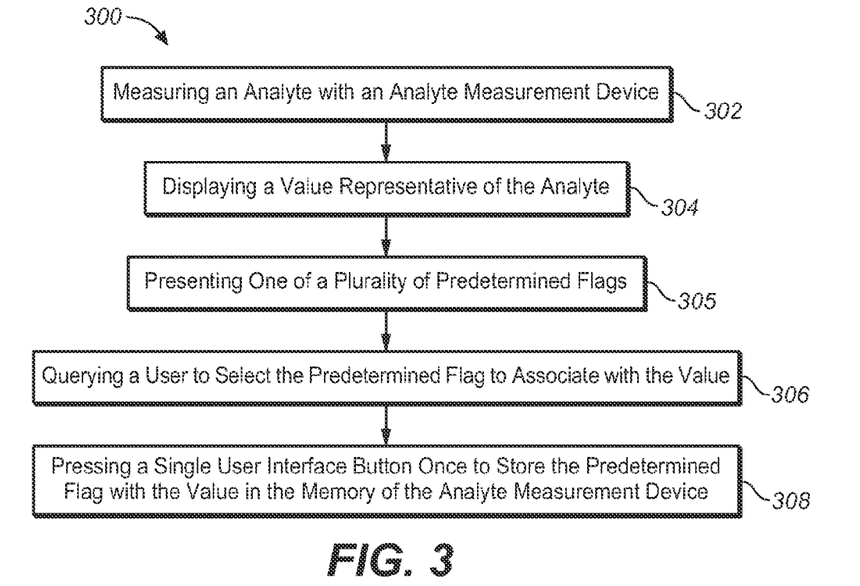
FIG. 3 is an exemplary flow chart illustrating a method of operating an analyte measurement device, according to an embodiment.

FIG. 3 is an exemplary flow chart illustrating a method of operating an analyte measurement device. Method 300 comprises steps 302, 304, 305, 306, and 308. In step 302, an analyte measuring device measures an analyte. In step 304, the analyte measuring device displays a value representative of the analyte. In step 305, the analyte measuring device presents one of a plurality of predetermined flags. In step 306, the analyte measuring device queries the user to select a predetermined flag to associate with the displayed value. In step 308, a single user interface button is pressed once, causing the predetermined flag and the displayed value to be stored in the memory of the analyte measurement device. In any embodiment described and illustrated herein, the analyte measurement device may include a display, a user interface, a processor, a memory and user interface buttons. In any embodiments described and illustrated herein, querying may include repetitively flashing on the display an icon representative of one of the user interface buttons to prompt a selection of such user interface button. In any embodiment described and illustrated herein, the icon may be selected from a group consisting of a first triangle and a second triangle having a smaller area than the first triangle.

Figure 4:
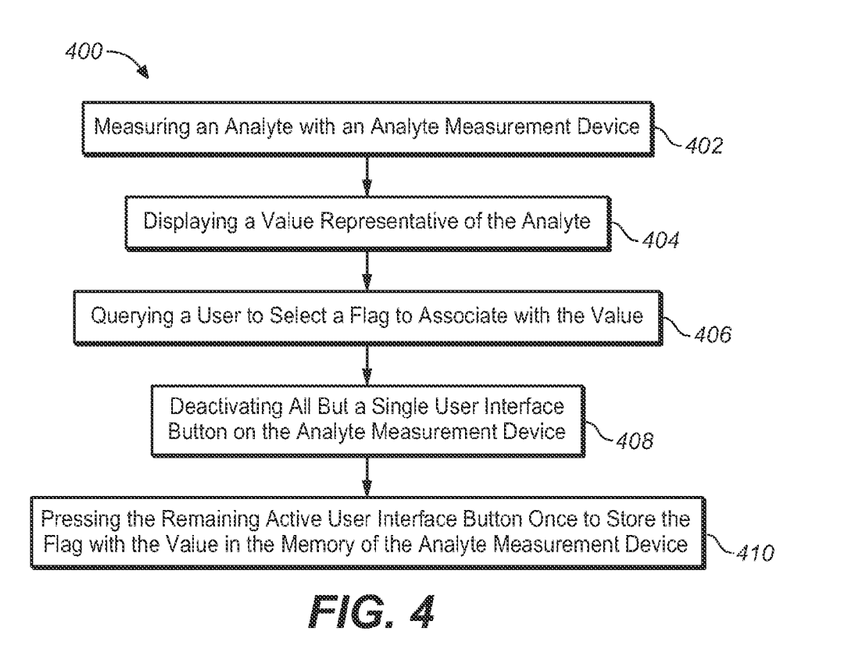
FIG. 4 is an exemplary flow chart illustrating a method of operating an analyte measurement device when only a single user interface button on the analyte measurement device is active, according to an embodiment.

FIG. 4 is an exemplary flow chart illustrating a method of operating an analyte measurement device when only a single user interface button on the analyte measurement device is active. Method 400 comprises steps 402, 404, 406, 408, and 410. In step 402, an analyte measuring device measures an analyte. In step 404, the analyte measuring device displays a value representative of the analyte. In step 406, the analyte measuring device queries the user to select a flag to associate with the displayed value. In step 408, the analyte measuring device deactivates all but a single user interface button. In step 410, the active user interface button is pressed once, causing the flag and the displayed value to be stored in the memory of the analyte measurement device. In any embodiment described and illustrated herein, user interface buttons may include an "up" button, a "down" button, and an "enter" or "OK" button. In any embodiment described and illustrated herein, user selectable flags may include a before meal flag, an after meal flag, a fasting flag, or a blank flag. In any embodiment described and illustrated herein, queries may be used whenever a measuring step has been completed.

Figure 5:
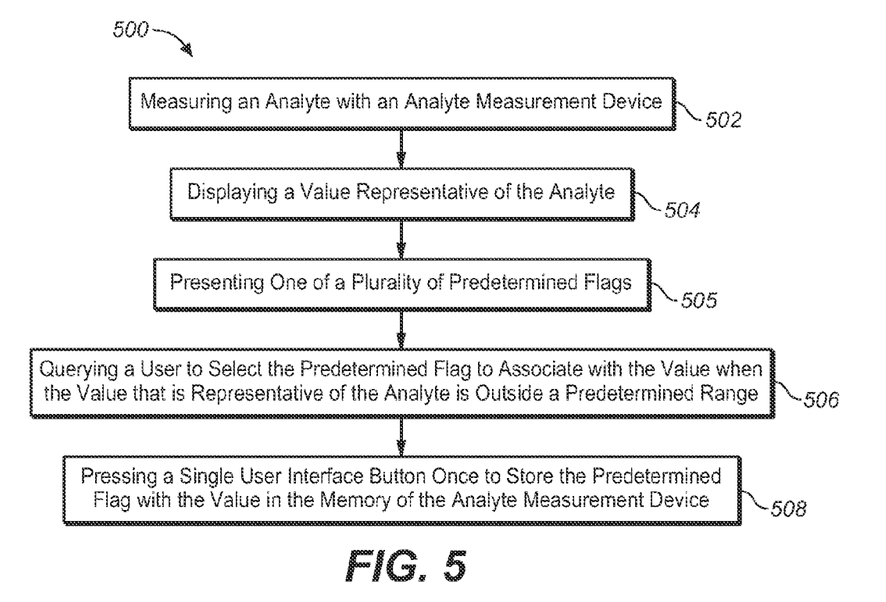
FIG. 5 is an exemplary flow chart illustrating a method of operating an analyte measurement device where a user is queried when an analyte value is outside a predetermined range, according to an embodiment.

FIG. 5 is an exemplary flow chart illustrating a method of operating an analyte measurement device where a user is queried when an analyte value is outside a predetermined range. Method 500 comprises steps 502, 504, 505, 506, and 508. In step 502, an analyte measuring device measures an analyte. In step 504, the analyte measuring device displays a value representative of the analyte. In step 505, the analyte measuring device presents one of a plurality of predetermined flags. In step 506, the analyte measuring device queries the user to select a predetermined flag to associate with the displayed value when the displayed value is outside a predetermined range. In step 508, a single user interface button is pressed once, causing the predetermined flag and the displayed value to be stored in the memory of the analyte measurement device.

Figure 6:
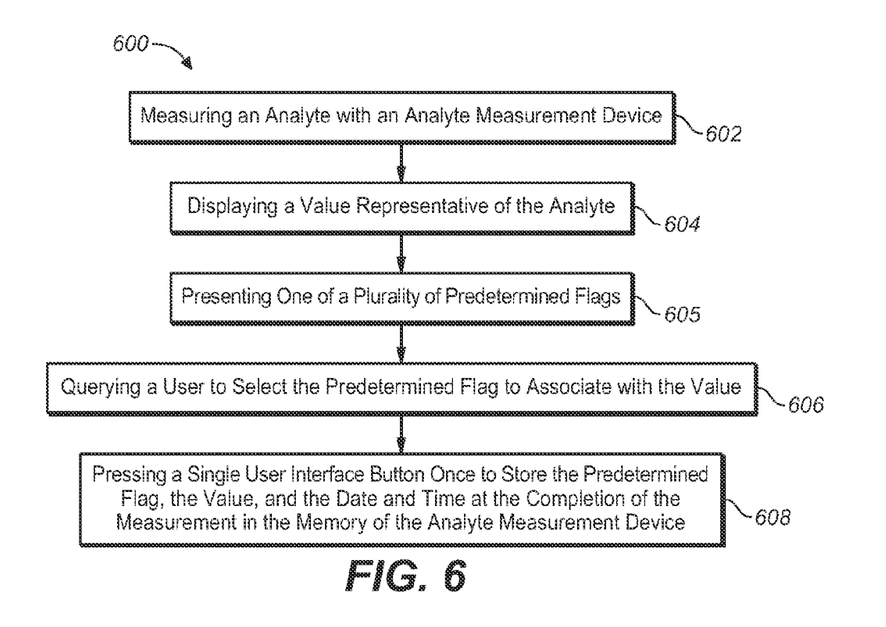
FIG. 6 is an exemplary flow chart illustrating a method of operating an analyte measurement device where a predetermined flag, an analyte value, and the date and time of a measurement are stored in the memory of the analyte measurement device, according to an embodiment.

FIG. 6 is an exemplary flow chart illustrating a method of operating an analyte measurement device where a predetermined flag, an analyte value, and the date and time of a measurement are stored in the memory of the analyte measurement device. Method 600 may include steps 602, 604, 605, 606, and 608. In step 602, an analyte measuring device measures an analyte. In step 604, the analyte measuring device displays a value representative of the analyte. In step 605, the analyte measuring device presents one of a plurality of predetermined flags. In step 606, the analyte measuring device queries the user to select a predetermined flag to associate with the displayed value. In step 608, a single user interface button is pressed once, causing the predetermined flag, the displayed value, and the date and time at the completion of the measurement to be stored in the memory of the analyte measurement device. In any embodiment described and illustrated herein, the analyte measuring device may include a glucose meter.

Figure 7:
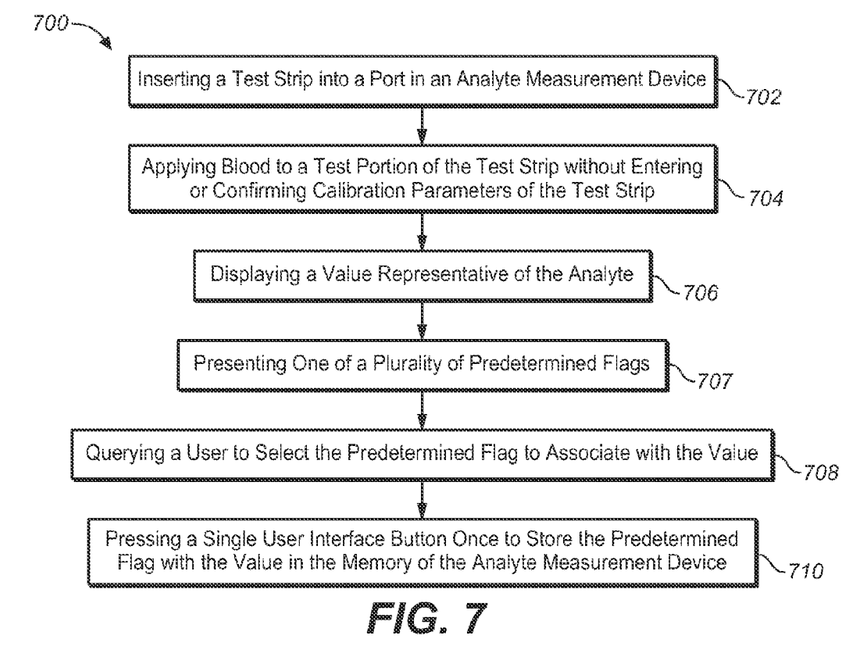
FIG. 7 is an exemplary flow chart illustrating a method of operating an analyte measurement device after inserting a test strip into a strip port in the analyte measurement device, according to an embodiment.

FIG. 7 is an exemplary flow chart illustrating a method of operating an analyte measurement device after inserting a test strip 10 into a strip port 113 in the analyte measurement device. Method 700 may include steps 702, 704, 706, 707, 708, and 710. In step 702, a test strip 10 is inserted into a strip port in an analyte measurement device. In step 704, blood is applied to a test portion (the portion distal from the strip port 112) of the test strip 10 without entering or confirming calibration parameters of the test strip 10. In step 706, the analyte measuring device displays a value representative of the analyte. In step 707, the analyte measuring device presents one of a plurality of predetermined flags. In step 708, the analyte measuring device queries the user to select a predetermined flag to associate with the displayed value. In step 710, a single user interface button is pressed once, causing the predetermined flag and the displayed value to be stored in the memory of the analyte measurement device. In any embodiment described and illustrated herein, measuring may include: inserting a test strip 10 into a strip port in the analyte measurement device, then depositing a sample of blood on a testing portion of the test strip 10 without entering a calibration parameter for the test strip 10.

Figure 8:
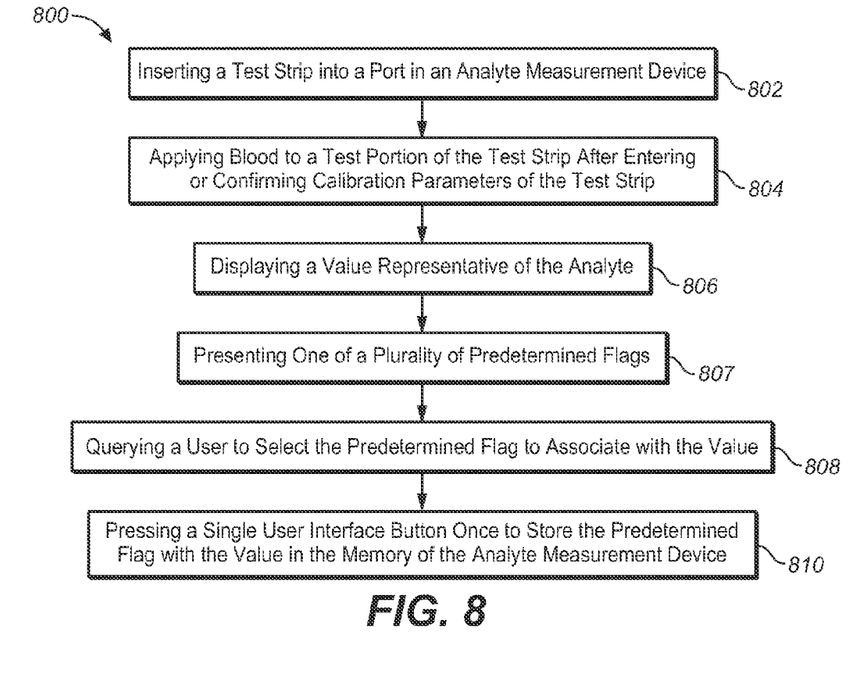
FIG. 8 is an exemplary flow chart illustrating a method of operating an analyte measurement device after inserting a test strip into a strip port in the analyte measurement device and either entering or confirming calibration parameters of the test strip, according to an embodiment.

FIG. 8 is an exemplary flow chart illustrating a method of operating an analyte measurement device after inserting a test strip 10 into a strip port in the analyte measurement device and either entering or confirming calibration parameters of the test strip 10. Method 800 may include steps 802, 804, 806, 807, 808, and 810. In step 802, a test strip 10 is inserted into a strip port in an analyte measurement device. In step 804, blood is applied to a test portion of the test strip 10 after entering or confirming calibration parameters of the test strip 10. In step 806, the analyte measuring device displays a value representative of the analyte. In step 807, the analyte measuring device presents one of a plurality of predetermined flags. In step 808, the analyte measuring device queries the user to select a predetermined flag to associate with the displayed value. In step 810, a single user interface button is pressed once, causing the predetermined flag and the displayed value to be stored in the memory of the analyte measurement device. In any embodiment described and illustrated herein, measuring may include: inserting a test strip 10 into a strip port in the measurement device; inputting a calibration parameter for the test strip 10 via the user interface buttons of the device; and depositing a blood sample on a testing portion of the test strip 10.

Figure 9:
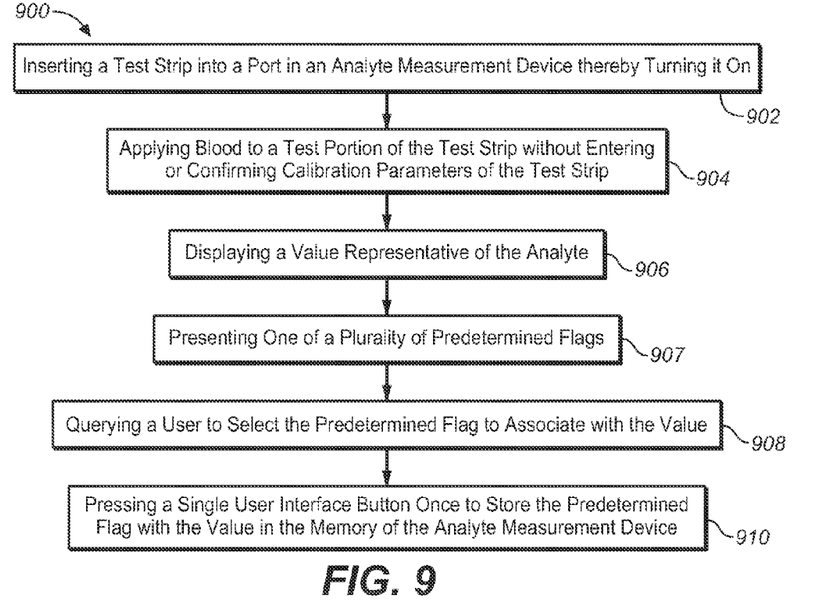
FIG. 9 is an exemplary flow chart illustrating a method of operating an analyte measurement device after inserting a test strip into a strip port in the analyte measurement device thereby turning the analyte measurement device on, according to an embodiment.

FIG. 9 is an exemplary flow chart illustrating a method of operating an analyte measurement device after inserting a test strip 10 into a strip port in the analyte measurement device thereby turning the analyte measurement device on. Method 900 may include steps 902, 904, 906, 907, 908, and 910. In step 902, a test strip 10 is inserted into a strip port in an analyte measurement device, thereby turning it on. In step 904, blood is applied to a test portion of the test strip 10 without entering or confirming calibration parameters of the test strip 10. In step 906, the analyte measuring device displays a value representative of the analyte. In step 907, the analyte measuring device presents one of a plurality of predetermined flags. In step 908, the analyte measuring device queries the user to select a predetermined flag to associate with the displayed value. In step 910, a single user interface button is pressed once, causing the predetermined flag and the displayed value to be stored in the memory of the analyte measurement device. In any embodiment described and illustrated herein, inserting may include turning on the measurement device when the strip is fully inserted into the strip port. In any embodiment described and illustrated herein, one of a plurality of user selectable predetermined flags may be selected from a group consisting essentially of at least one of a comment title, a plurality of comments, comment page number, no comment, not enough food, too much food, mild exercise, strenuous exercise, medication, stress, illness, hypoglycemic state, menses, vacation, and combinations thereof. In any embodiment described and illustrated herein, a plurality of menus may be displayed. In any embodiment described and illustrated herein, one of a plurality of menus may include a prompt for last result, all results, result average, and set up. In any embodiment described and illustrated herein, a plurality of menus may include a display of a prompt for all results average, before meal average, after meal average.

Figure 10:
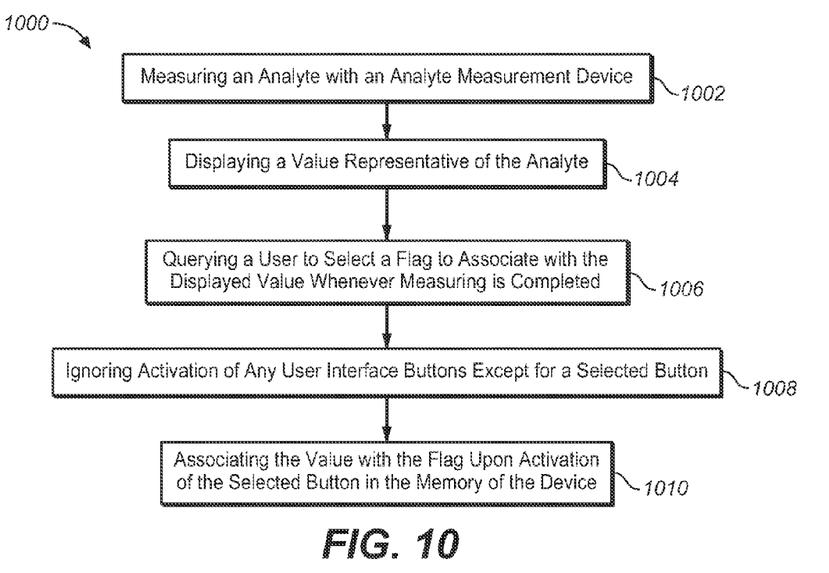
FIG. 10 is an exemplary flow chart illustrating an alternative method of operating an analyte measurement device where all but one user interface buttons are ignored

In an alternative embodiment, certain keys on the meter can be disabled or ignored to ensure simplicity in the operation of the device. For example, in FIG. 10, all but one user interface buttons are ignored. Method 1000 may include steps 1002, 1004, 1006, 1008, and 1010. In step 1002, an analyte measuring device measures an analyte. In step 1004, the analyte measuring device displays a value representative of the analyte. In step 1006, the analyte measuring device queries the user to select a flag to associate with the displayed value whenever measuring is completed. In step 1008, the analyte measuring device ignores activation of all but a single user interface button. In step 1010, the single non-ignored user interface button is pressed once, causing the flag and the displayed value to be stored in the memory of the analyte measurement device.

Figure 11:
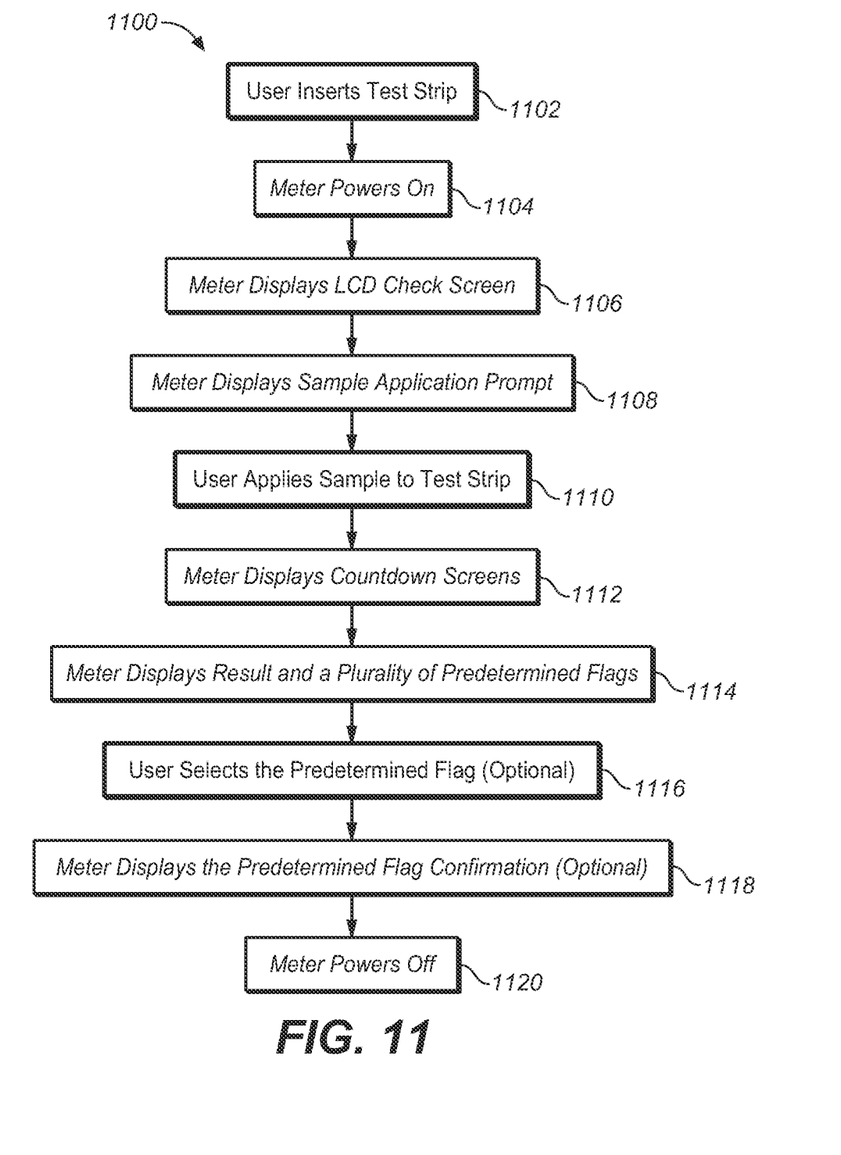
FIG. 11 is an exemplary flow chart illustrating a method of operating an analyte measurement device and actions taken by the analyte measurement device, according to an embodiment.

FIG. 11 is an exemplary flow chart illustrating a method of operating an analyte measurement device and actions taken by the analyte measurement device. Method 1100 may include steps 1102, 1104, 1106, 1108, 1110, 1112, 1114, 1116, 1118, and 1120. In step 1102, a user inserts a test strip 10 into a strip port in an analyte measurement device. In step 1104, the analyte measuring device turns on. In step 1106, the analyte measuring device displays an LCD check screen. In step 1108, the analyte measuring device displays a sample application prompt. In step 1110, the user applies sample to the test strip 10. In step 1112, the analyte measuring device displays a series of countdown screens. In step 1114, the analyte measuring device displays a value representative of the analyte and queries the user to select one of a plurality of predetermined flags to associate with the displayed value. In step 1116, the user selects a predetermined flag, causing the predetermined flag and the displayed value to be stored in the memory of the analyte measurement device. In step 1118, the analyte measurement device displays a predetermined flag confirmation. In step 1120, the analyte measurement device turns off after a predetermined time, without interaction from the user.

Figure 12:
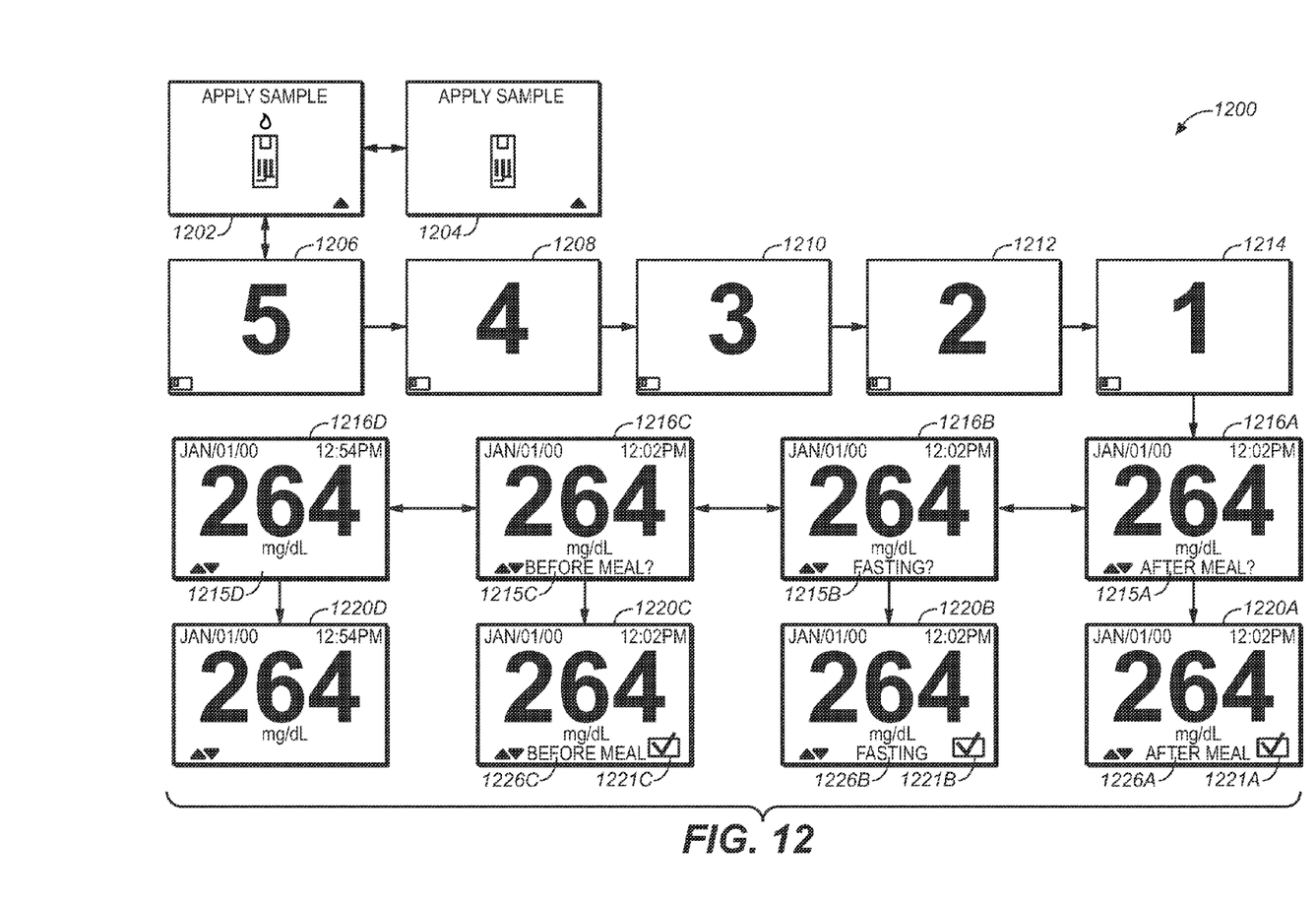
FIG. 12 illustrates a series of user interface screens used in a method of operating an analyte measurement device, according to an embodiment.

FIG. 12 illustrates a series of user interface screens displayed during a method of operating an analyte measurement device. Method 1200 may include screens 1202, 1204, 1206,

1208, 1210, 1212, 1214, 1216A, 1216B, 1216C, 1216D, 1220A, 1220B, 1220C, and 1220D. In screens 1202 and 1204, the user is prompted to apply sample to a test strip 10 that has been inserted into a strip port in an analyte measurement device. In screen 1202 an icon symbolizing a drop of blood is displayed, while in screen 1204 there is no icon symbolizing a drop of blood. Screens 1202 and 1204 are alternated, creating the impression of a blinking drop of blood. Once sample is applied to the test strip 10, screens 1206, 1208, 1210, 1212, and 1214 are displayed, in succession. Screens 1206 through 1214 provide a countdown to result that is approximately 5 seconds in duration. In screens 1216A through 1216D, the analyte measuring device displays a value representative of the analyte and queries the user to select one of a plurality of predetermined flags to associate with the displayed value. A user can alternate between screens 1216A through 1216D by pressing a user interface button, such as the up button or the down button. Screen 1216A may include after meal flag 1215A, screen 1216B may include fasting flag 1215B, screen 1216C may include before meal flag 1215C, and screen 1216D may include blank flag 1215D. Any one of flags 1215A through 1215D can be selected by pressing a user interface button (such as, for example, an OK button) while the flag is displayed. Once a flag is selected, one of screens 1220A through 1220D is displayed. Screen 1220A is displayed when after meal flag 1215A is selected, screen 1220B is displayed when fasting flag 1215B is selected, screen 1220C is displayed when before meal flag 1215C is selected, and screen 1220D is displayed when blank flag 1215D is selected. Screens 1220A through 1220C include confirmation icons 1221A through 1221C, indicating that the corresponding flag has been selected. In any embodiments described and illustrated herein, querying may include repetitively flashing on the display an icon representative of a single user interface button to prompt selection of the single user interface button.

Figure 13:
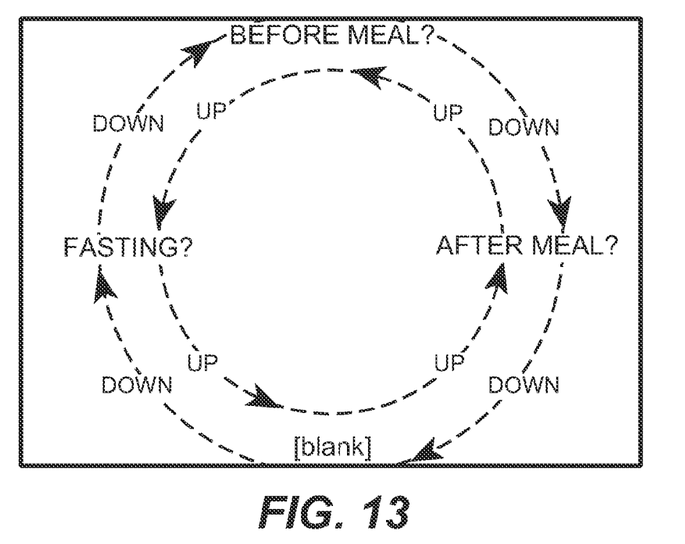
FIG. 13 illustrates various navigation paths for the selection of various predetermined flags.

Referring to FIG. 13, the flags can be selected by using the up and down keys of the meter. Alternatively, the various flags can be automatically displayed for selection as a default flag depending on when a blood glucose measurement is taken during various time periods in a day. For example, in one embodiment, a "fasting" flag can be set as a default flag automatically whenever a measurement is taken in the early morning period as determined by the internal clock of the meter 100. A "before meal" flag can be the default flag displayed upon the measurement around certain time periods near meal times. Likewise, an "after meal" flag can be set to be displayed as a default flag for selection by the user whenever a measurement is taken at certain times of the day.

Figure 14A:
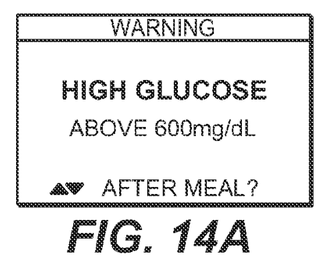
FIGS. 14A-14D illustrate various user interface screens that can be used to display respective warning messages instead of a numerical value for a blood glucose measurement along with a flag that can be associated with the warning message.
Figure 14B:
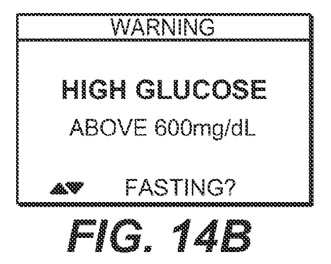
Figure 14C:
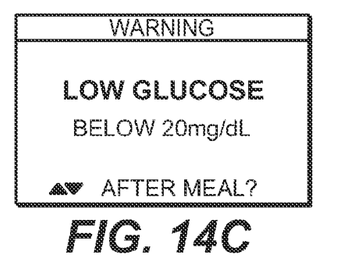
Figure 14D:
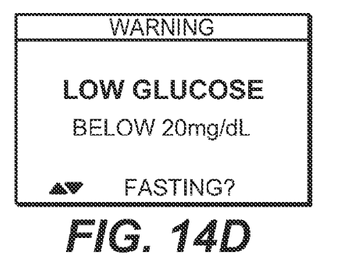

Referring to FIGS. 14A and 14B, where a measurement exceeds a certain range, a warning message can be displayed and a flag can be associated with such warning message. For example, in FIG. 14A, where the measurement exceeds a certain preset value for a test strip, a warning message of "High Glucose" is displayed. An appropriate flag can be automatically displayed or selected manually by the user as described above. In the example of FIG. 14A, an "After Meal" flag is displayed and a query in the form of a question mark is presented to the user. In FIG. 14B, a "fasting" flag can be displayed with a query for the selection of the flag to be associated with the measurement. FIGS. 14C and 14D illustrate a warning message with examples of the flags that can be associated with a low glucose value. As noted earlier, the time at which such measurement was taken along with the flag selected can be stored in memory for later retrieval by the user or a health care provider for later analysis.

Figure 15A:
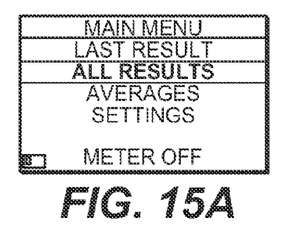
FIGS. 15A-15I illustrate various user interface screens to provide additional statistical information regarding blood glucose measurements.
Figure 15B:
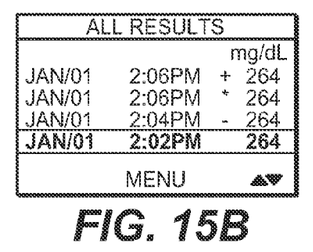

Referring to FIGS. 15A-15I, various screens can be accessed by the users or health care provider to provide statistical data utilized in the treatment of diabetes. As shown in FIG. 15A, a main menu screen allows a user to access various statistical data regarding the blood glucose measurement stored on the meter 100 along with various flags associated therewith, the time, date, year, and any other data useful in the treatment of diabetes.

For example, the meter can be configured to display the following screens in the main menu: "Last Result"; "All Results"; "Averages"; and "Settings." Where the "Last Result" screen is selected, the meter allows for accessing of the latest result stored in the meter; a selection of "All Results" screen allow for all glucose measurement results stored on the meter to be provided for a complete record to the user, shown here in FIG. 15B where display screen size permitting, four or more results can be displayed at one time; the average of blood glucose data associated with a specific flag can also be obtained with selection of the "Averages" screen.

Figure 15C:
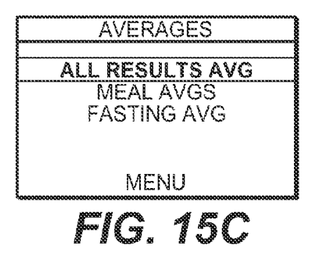
Figure 15D:
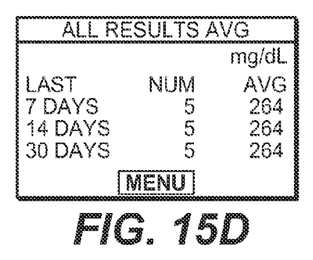
Figure 15E:
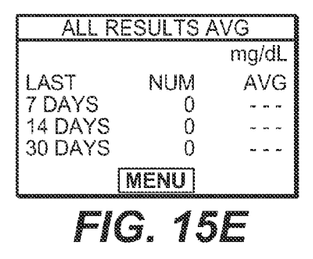

Referring to FIG. 15C, an "All Results Average" menu can be selected to provide, for example, an average of all blood glucose results stored in the meter. Alternatively, the screen can be configured to provide for a median value of the blood glucose value from all of the results stored in the meter instead of an average. Where this screen is highlighted and selected in FIG. 15C, a screen, shown in FIG. 15D is displayed showing various averages by different categories such as, for example, within the last 7, 14, or 30 days and the average (or median) of the blood glucose value within each time period (e.g., date time year) and whether such value was before ("BFR") or after ("AFT") a meal. Where there are not enough data to display the average in the various time periods, the display will shown, as in FIG. 15E, dashed lines indicating insufficient data.

Figure 15F:
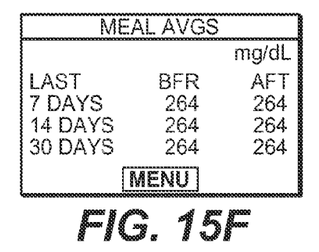
Figure 15G:
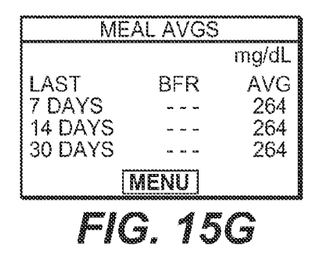

Referring to FIG. 15C where the "Meal Averages" screen is selected, the display is configured to display, as shown here in FIG. 15F of the meal averages (or median) of the measured glucose value by different time periods and whether the average was before or after a meal. Again, where there is insufficient data, the screen will display dashed lines indicating the same in FIG. 15G.

Figure 15H:
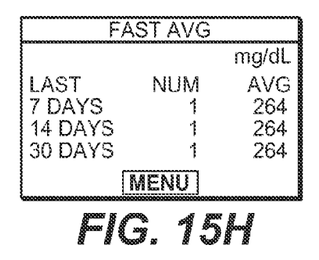
Figure 15I:
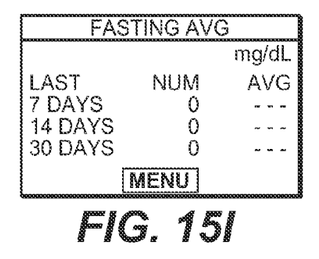

The fasting average of blood glucose measured can also be obtained by selecting the "Fasting Average" screen in FIG. 15C by the user, which would then be shown in FIG. 15H in various time periods. As before, the meter can display the median instead of average glucose value. Where there is insufficient data, the display will indicate the same by a series of dashed lines as shown in FIG. 15I.

In conclusion, the testing device and methods described and illustrated herein significantly reduce obstacles associated with maintaining an accurate record of an individual's blood glucose testing and lifestyle. The various embodiments of the present invention is believed to promote frequent monitoring for diabetic individuals by providing a simple, efficient way of recording not only blood glucose levels, but other information which is likely to affect an individual's prognosis. By logging glucose and lifestyle information in the manner described herein, the testing device and methods described and illustrated herein provide an effective record keeping system.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of operating an analyte measurement device having a display, user interface, processor, memory and user interface buttons, the method comprising:
   measuring an analyte with the analyte measurement device;
   displaying a value representative of the analyte;
   automatically displaying by the analyte measurement device one of a plurality of predetermined flags that includes a before meal flag, an after meal flag, a fasting flag, or a blank flag depending on when the measuring step is taken during a day by the analyte measurement device, including a fasting flag being set as a default flag whenever a measurement is taken in an early morning period as determined by an internal clock of the measurement device and further including before meal or after meal flag set as a default flag near meal times as determined by the internal clock of the measurement device;
   querying a user to select the one predetermined flag shown on the display by the displaying step to associate the one predetermined flag with the value; and
   pressing only one of the user interface buttons once to store the one predetermined flag with the value of the analyte in the memory of the device.

2. The method of claim 1, in which the user interface buttons comprise an up button, a down button and an OK button.

3. The method of claim 1, in which the querying comprises pressing a user interface button to select another of the plurality of predetermined flags.

4. The method of claim 1, in which the querying comprises always querying a user whenever a measuring step has been completed.

5. The method of claim 1, in which the querying comprises querying a user whenever a measuring step indicates that an analyte value is outside a predetermined range.

6. The method of claim 1, in which the pressing comprises storing in memory the date and time at the completion of the measuring step with the selected flag.

7. The method of claim 1, in which the analyte measurement device comprises a glucose meter.

8. The method of claim 1, in which the measuring comprises:
   inserting a test strip into a strip port provided by the measurement device; and
   depositing a blood sample on a testing portion of the test strip without entering a calibration parameter for the test strip.

9. The method of claim 1, in which the measuring comprises
   inserting a test strip into a strip port provided by the measurement device;
   inputting a calibration parameter for the test strip via the user interface buttons of the device; and,
   depositing a blood sample on a testing portion of the test strip.

10. The method of claim 9, in which the inserting comprises turning on the measurement device when the strip is fully inserted into the strip port.

11. The method of claim 1, in which the plurality of predetermined flags comprise a comment title, a plurality of comments, comment page number, no comment, not enough food, too much food, mild exercise, strenuous exercise, medication, stress, illness, hypoglycemic state, menses, vacation, and combinations thereof.

12. The method of claim 1, further comprising selecting a plurality of menus to be displayed.

13. The method of claim 12, in which one of the plurality of menus comprises a prompt for last result, all results, averages, and settings.

14. The method of claim 13, in which another of the plurality of menus comprises a prompt for all results average, meal averages, and fasting averages.

15. The method of claim 1, in which the displaying comprises exhibiting a message of a value less than a predetermined value.

16. The method of claim 1, in which the displaying comprises exhibiting a message of a value higher than a predetermined value.

17. The method of one of claim 15 or claim 16, in which the pressing comprises storing the predetermined flag with the message.

18. A method of operating an analyte measurement device having a display, user interface, processor, memory and user interface buttons, the method comprising:
   measuring an analyte with the analyte measurement device;
   displaying a value representative of the analyte;
   presenting a default flag from a plurality of predetermined flags depending on when the measuring step is taken at various time periods in a day, the presenting including displaying a fasting flag as a default flag whenever a measurement is taken in an early morning period as determined by an internal clock of the measurement device and further displaying before meal or after meal flag set as a default flag near meal times as determined by the internal clock of the measurement device;
   querying a user to select the default flag to associate the default flag with the value; and
   pressing only one of the user interface buttons once to store the default flag with the value of the analyte in the memory of the device.

19. The method of claim 18, in which the default flag comprises a before meal flag near meal times during a day.

20. The method of claim 18, in which the default flag comprises an after meal flag near meal times during a day.

* * * * *